United States Patent
Herman et al.

(10) Patent No.: US 10,181,212 B2
(45) Date of Patent: Jan. 15, 2019

(54) METHOD AND SYSTEM FOR REDUCING MOTION SICKNESS IN VIRTUAL REALITY RIDE SYSTEMS

(71) Applicant: DreamWorks Animation LLC, Glendale, CA (US)

(72) Inventors: Brad Kenneth Herman, Culver City, CA (US); Shiraz Akmal, Glendale, CA (US); Bryn Lafollette, Glendale, CA (US)

(73) Assignee: DreamWorks Animation L.L.C., Universal City, CA (US)

( * ) Notice: Subject to any disclaimer, the term of this patent is extended or adjusted under 35 U.S.C. 154(b) by 0 days.

(21) Appl. No.: 14/704,922

(22) Filed: May 5, 2015

(65) Prior Publication Data
US 2015/0325027 A1 Nov. 12, 2015

Related U.S. Application Data

(60) Provisional application No. 61/991,358, filed on May 9, 2014.

(51) Int. Cl.
*G02B 27/01* (2006.01)
*G06T 13/00* (2011.01)
(Continued)

(52) U.S. Cl.
CPC ............. *G06T 13/00* (2013.01); *A61M 21/00* (2013.01); *A63F 13/211* (2014.09);
(Continued)

(58) Field of Classification Search
CPC .. A61M 2021/0011; A61M 2021/0022; A61M 2021/0027; A61M 2021/005;
(Continued)

(56) References Cited

U.S. PATENT DOCUMENTS

| 5,695,406 A | 12/1997 | Park |
| 2005/0219206 A1* | 10/2005 | Schena ................ G06F 3/016 345/156 |

(Continued)

FOREIGN PATENT DOCUMENTS

| WO | 2010/101641 A2 | 9/2010 |
| WO | 2013/059560 A1 | 4/2013 |

OTHER PUBLICATIONS

J. Plouzeau, et al., "Vibrations in dynamic driving simulator: Study and implementation", CONFERE 2013, Jul. 2013, France, p. 1-8.*

(Continued)

*Primary Examiner* — Jin Cheng Wang
(74) *Attorney, Agent, or Firm* — Dentons US LLP

(57) ABSTRACT

A virtual reality ride system including a headset, a control unit, and a dynamic platform. The headset includes a display unit configured to display a video of an animated virtual environment. The control unit includes one or more processors configured to perform render processing that renders the video of the virtual environment; event motion processing that generates first data representing motions associated with events in the virtual environment; and low-frequency motion processing that generates second data representing low-frequency vibrations unrelated to the events in the virtual environment. The dynamic platform is configured to produce the motions associated with the events in the virtual environment based on the first data, and to produce the low-frequency vibrations based on the second data. The low-frequency vibrations include a frequency between about 5 Hz and 70 Hz.

21 Claims, 11 Drawing Sheets

(51) Int. Cl.

| | | |
|---|---|---|
| *G06T 19/00* | (2011.01) | |
| *G06F 3/01* | (2006.01) | |
| *A61M 21/00* | (2006.01) | |
| *B60W 40/08* | (2012.01) | |
| *A63F 13/25* | (2014.01) | |
| *A63F 13/428* | (2014.01) | |
| *A63F 13/211* | (2014.01) | |
| *A63F 13/212* | (2014.01) | |
| *A63F 13/28* | (2014.01) | |

(52) U.S. Cl.
CPC ............ *A63F 13/212* (2014.09); *A63F 13/25* (2014.09); *A63F 13/28* (2014.09); *A63F 13/428* (2014.09); *B60W 40/08* (2013.01); *G02B 27/017* (2013.01); *G06F 3/016* (2013.01); *G06T 19/006* (2013.01); *A61M 2021/005* (2013.01); *A61M 2021/0011* (2013.01); *A61M 2021/0022* (2013.01); *A61M 2021/0027* (2013.01); *A61M 2205/332* (2013.01); *A61M 2205/507* (2013.01); *A61M 2205/70* (2013.01)

(58) Field of Classification Search
CPC ............ A61M 21/00; A61M 2205/332; A61M 2205/507; A61M 2205/70; B60W 40/08; G02B 27/017; G02B 2027/0187; G02B 207/02832; G06F 3/016; G06T 13/00; G06T 19/006; G06T 3/011

USPC ........................................................ 345/633
See application file for complete search history.

(56) References Cited

U.S. PATENT DOCUMENTS

| | | | | |
|---|---|---|---|---|
| 2015/0068052 | A1* | 3/2015 | Krueger | ................... G01C 9/16 33/301 |
| 2015/0097860 | A1* | 4/2015 | Alaniz | .................... G06F 3/011 345/633 |
| 2015/0123624 | A1* | 5/2015 | Ookawa | ................ B60W 30/02 322/22 |

OTHER PUBLICATIONS

L. Lei, et al. "Analyses of Vehicle Vibration Based on Virtual Reality", retrieved from http://bmas.designers-guide.org/2005/web-only-pubs/BMAS2005_13.pdf, 2005, p. 1-6.*
Nick Coates, et al., "Head-Mounted Display in Driving Simulation Applications in Cards", DSC2002, Paris, Sep. 2002, pp. 33-43.*
Markus von der Heyde, "A Distributed Virtual Reality System for Spatial Updating: Concepts, Implementation, and Experiments", MPI Series in Biological Cybernetics, No. 02, Jan. 2001 (PhD Thesis, Sep. 19, 2000), pp. 1-117.*
Extended European Search Report received for European Patent Application No. 15166393.7, dated Nov. 19, 2015, 8 pages.

* cited by examiner

METHOD AND SYSTEM FOR REDUCING MOTION SICKNESS IN VIRTUAL REALITY RIDE SYSTEMS

CROSS-REFERENCE TO RELATED APPLICATIONS

This application claims the benefit of U.S. Provisional Application No. 61/991,358, filed May 9, 2014, which is hereby incorporated by reference in its entirety.

BACKGROUND

1. Field

This application relates generally to virtual reality ride systems, and, more specifically, to methods and systems using low-frequency vibrations to reduce motion sickness caused by virtual reality.

2. Description of the Related Art

Virtual reality is a computer-simulated environment that can simulate a user's physical presence in real or imaginary environments. A virtual reality environment may include visual images displayed either on a computer screen or through a stereoscopic (e.g., 3D) display, such as a wearable headset. The virtual reality environment may also include sound provided through speakers or headphones and force feedback via, for example, a dynamic platform or a vibrating controller or joystick. Applications of virtual reality include medical, gaming, and military environments.

Although virtual reality systems may provide a realistic and immersive experience, they also cause motion sickness in many users. Motion sickness may occur when the systems of the body responsible for balance do not agree with each other. The three bodily systems primarily responsible for balance are the visual system (including the eyes), proprioception (the sense of movement and relative position of various parts of the body by the musculoskeletal system), and the vestibular system located in the inner ear. The vestibular system includes three semicircular canals and two otolith organs. The canals are oriented in three spatial planes and sense angular acceleration, while the otolith organs sense linear acceleration and the position of the head relative to gravity. The brain combines information from proprioception and from the vestibular system into its overall sense of body position, movement, and acceleration. Visual signals regarding the body's position in relation to its surroundings are processed by the brain and compared to information from the vestibular and musculoskeletal systems.

Visually induced motion sickness occurs when motion is perceived visually but the body is physically at rest, is not feeling forces from acceleration, or is not physically experiencing motion consistent with the visually perceived motion. When this happens, there is a disconnect between the motion perceived by the visual system and the physical motion (or lack thereof) sensed by the proprioception and the vestibular systems. A person may experience visually induced motion sickness when, for example, viewing a first-person perspective of a moving scene, such as in a video game or a flight simulator.

Motion sickness caused by computer images, video games, simulators, or virtual reality may be referred to as simulation sickness. Simulation sickness is typically associated with situations in which a person generally is not moving, which distinguishes it from other types of motion sickness that occurs when a person is in motion (e.g., car sickness or sea sickness).

Symptoms of motion sickness may include dizziness, fatigue, nausea, headaches, drowsiness, sweating, and vomiting. Moreover, motion sickness may be even more severe during a virtual reality experience in which all external reference points that could provide a frame of reference are blocked from vision and the simulated images are 3D, such as when a 3D headset is used.

SUMMARY

The present disclosure describes a virtual reality ride system and method that reduce motion sickness associated with a virtual reality experience. The virtual reality ride system includes a dynamic platform that vibrates at a low frequency. The vibrations may be nearly or completely unnoticeable to the rider, but are detected by the vestibular system, reducing confusion between the visual and vestibular systems.

In one embodiment, a virtual reality ride system includes a headset, a control unit, and a dynamic platform. The headset includes a display unit configured to display a video of an animated virtual environment. The control unit includes one or more processors configured to perform render processing that renders the video of the virtual environment; event motion processing that generates first data representing motions associated with events in the virtual environment; and low-frequency motion processing that generates second data representing low-frequency vibrations unrelated to the events in the virtual environment. The dynamic platform is configured to produce the motions associated with the events in the virtual environment based on the first data, and to produce the low-frequency vibrations based on the second data. The low-frequency vibrations include a frequency between about 5 Hz and 70 Hz. The dynamic platform may include a seat or a bench. The low-frequency vibrations may reduce motion sickness that is induced by the displayed video.

In some embodiments, the low-frequency vibrations are not perceptible to a human sense of hearing or to a human sense of touch. In another embodiment, the video is three-dimensional. In yet another embodiment, the video shows a first-person perspective of the virtual environment.

In one embodiment, a method of generating a virtual reality ride includes: rendering a video of an animated virtual environment that includes virtual events; determining movements for a dynamic platform, where the movements are associated with the virtual events; determining low-frequency vibrations for the dynamic platform, where the low-frequency vibrations have a frequency between about 5 Hz and 70 Hz, and are unrelated to the virtual events; displaying the video on a display; and moving the dynamic platform, in synchronization with displaying the video, according to the determined movements and low-frequency vibrations. The vibrations may reduce motion sickness that is induced by the displayed video.

In another embodiment, a non-transitory computer-readable storage medium includes computer-executable instructions for generating a virtual reality ride. The computer-executable instructions include instructions for: rendering a video of an animated virtual environment that includes virtual events; determining movements for a dynamic platform, where the movements are associated with the virtual events; determining low-frequency vibrations for the dynamic platform, where the low-frequency vibrations have a frequency between about 5 Hz and 70 Hz, and are unrelated to the virtual events; displaying the video on a display; and moving the dynamic platform, in synchronization with displaying the video, according to the determined movements and low-frequency vibrations. The vibrations may reduce motion sickness that is induced by the displayed video.

The embodiments depicted in the figures are only exemplary. One skilled in the art will readily recognize from the following discussion that alternative embodiments of the structures and methods illustrated herein can be employed without departing from the principles described herein.

DETAILED DESCRIPTION

The following description sets forth specific configurations, parameters, and the like. It should be recognized, however, that such description is not intended to limit the present disclosure, but is instead provided as a description of exemplary embodiments.

Figure 1:
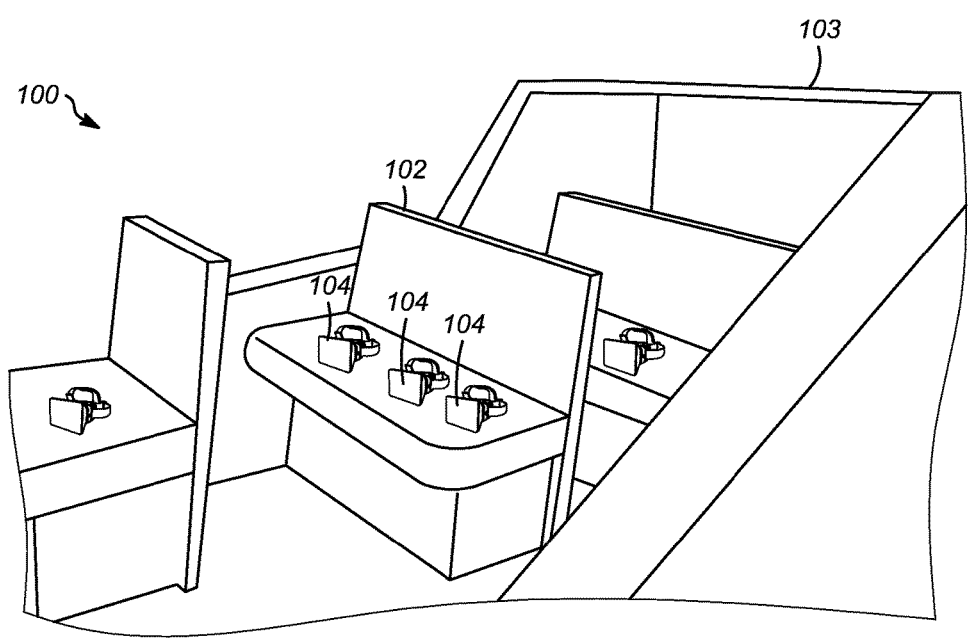
FIG. 1 depicts an exemplary embodiment of a virtual reality ride system.

FIG. 1 depicts an embodiment of a virtual reality ride system 100 including dynamic platform 102 and virtual reality headsets 104. Each headset 104 displays a video image, which may include, for example, a video of an animated virtual environment. The dynamic platform 102 may move to provide physical sensations associated with the visual events occurring in the virtual environment seen by the rider. A surrounding structure 103 may include walls, doors, windows, lights, or other features associated with the type of virtual reality ride. For example, a ride showing a virtual flight may have a structure resembling an airplane. In addition, virtual reality ride system 100 may provide audio to accompany the visual imagery of the headset 104 and the motion of the dynamic platform 102.

As discussed in greater detail below, the dynamic platform 102 may also vibrate at a low frequency with enough amplitude to stimulate the vestibular system of a rider and reduce motion sickness. For the purposes of this disclosure, motion sickness includes simulation sickness caused by virtual reality, video games, simulations, or the like.

Figure 2A:
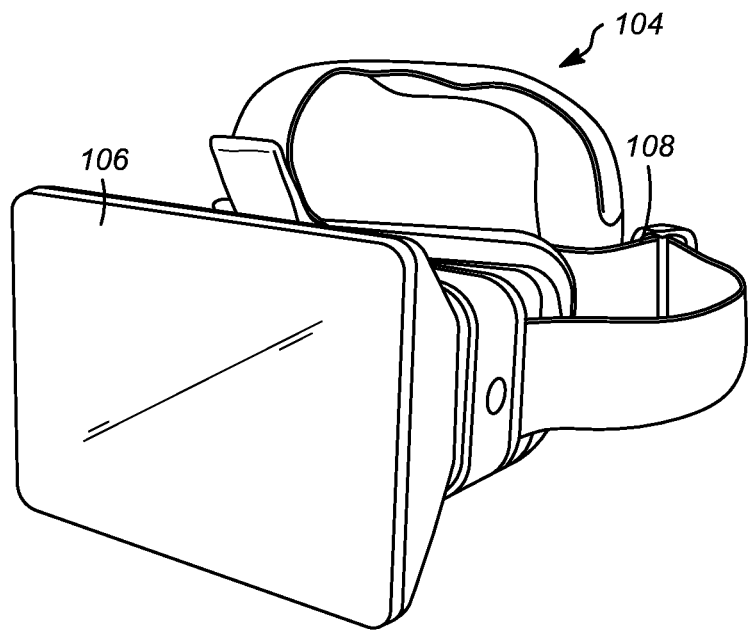
FIGS. 2A-2B depict an exemplary embodiment of a virtual reality headset.
Figure 2B:
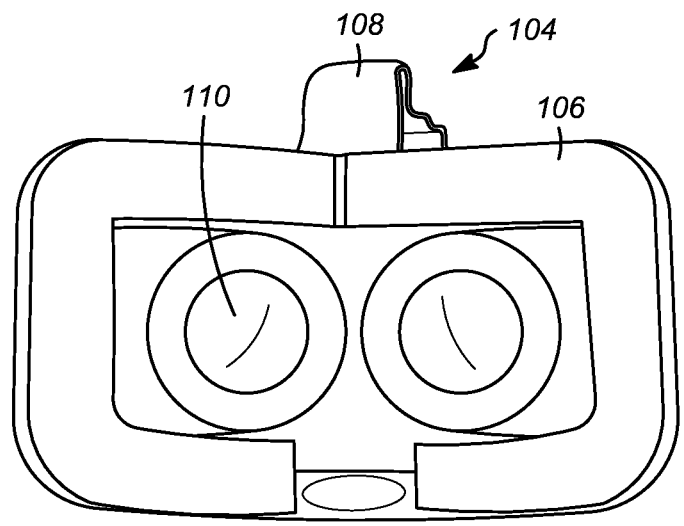

FIGS. 2A-2B depict an enlarged view of an exemplary virtual reality headset 104. The headset 104 includes a display/sensor portion 106 and straps 108 to secure the headset 104 to the rider's head. The display/sensor portion 106 includes a display unit that generates a two-dimensional or three-dimensional representation of the virtual environment. The virtual environment may be displayed by projecting an image onto a miniaturized screen in the headset 104. In some embodiments, the display unit may include a CRT, LEDs, LCDs, or the like. Optics may be used to manipulate and condition the light from the display to be presented to the rider. As seen in FIG. 2B, for example, the headset includes binocular optics 110 for viewing the display.

The headset 104 may also include a motion-sensing unit that includes sensors—such as, for example, gyroscopes, accelerometers, or the like—to detect and track movement of the rider's head. The headset 104 may track translational movement in one, two, or three dimensions. The headset 104 may also track rotation about one, two, or three axes. By tracking translational and rotational motion, the position of the rider's head may be determined. For the purposes of this disclosure, position information may include location (e.g., linear position, such as the coordinates of an object along the x, y, and z axes of a rectilinear reference frame) and/or orientation (e.g., angular position, attitude, or the heading, elevation, and bank of an object relative to a fixed reference frame). The headset 104 may also include means for recalibration. For example, a magnetometer may be included to correct drift in gyroscopes used in the headset 104.

Figure 3A:
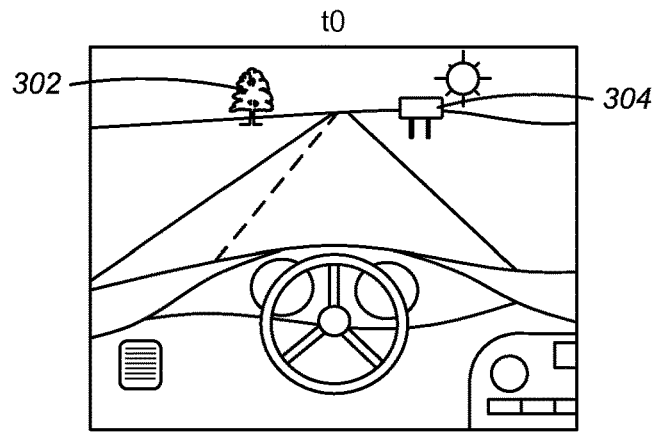
FIGS. 3A-3C depict an exemplary video of a virtual reality environment.
Figure 3B:
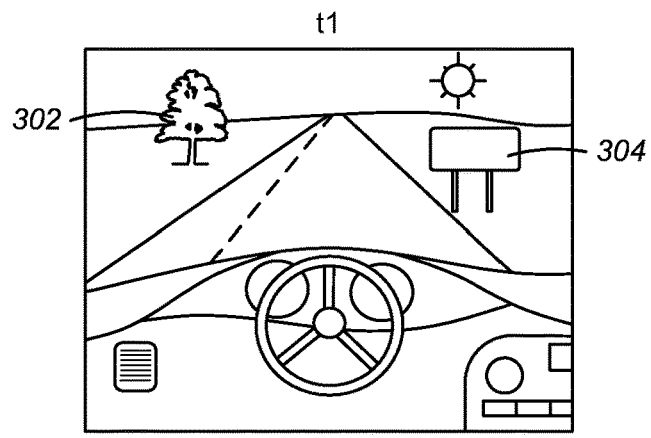
Figure 3C:
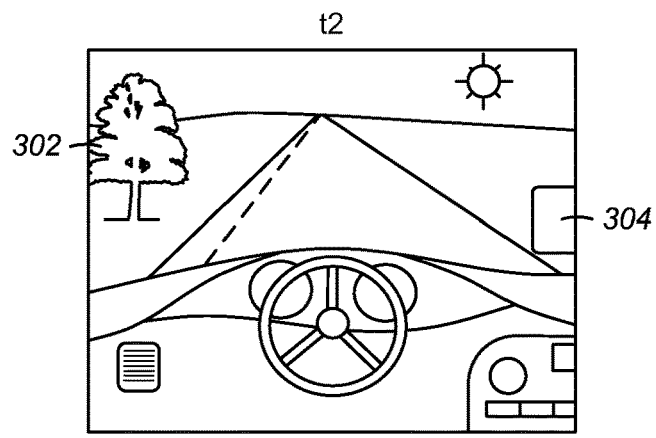

FIGS. 3A-3C depict an exemplary video of a virtual reality experience that may be displayed by the headset 104. The video depicted in FIGS. 3A-3C serves as an example of an experience in which low-frequency vibrations may be used to reduce motion sickness, including simulation sickness caused by the virtual reality experience.

As shown in FIG. 3A, the headset displays a video showing a first-person perspective of a virtual environment from the driver's seat of a car. FIGS. 3A-3C depict the virtual environment displayed at times t0, t1, and t2, respectively, where t0<t1<t2.

Figure 4A:
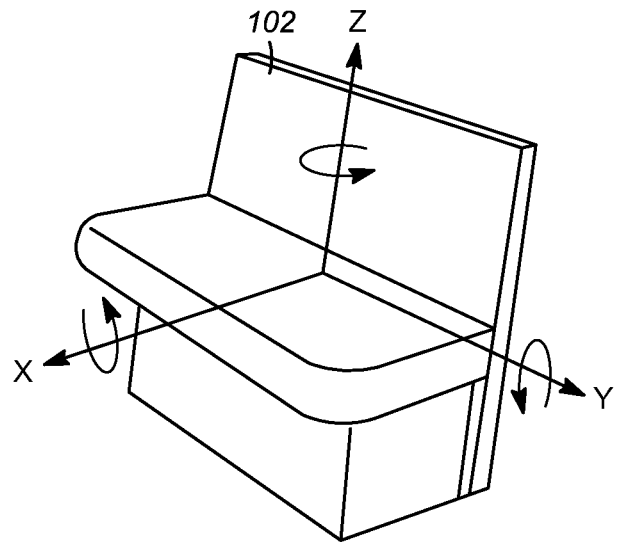
FIGS. 4A-4B depict an exemplary embodiment of a dynamic platform.
Figure 4B:
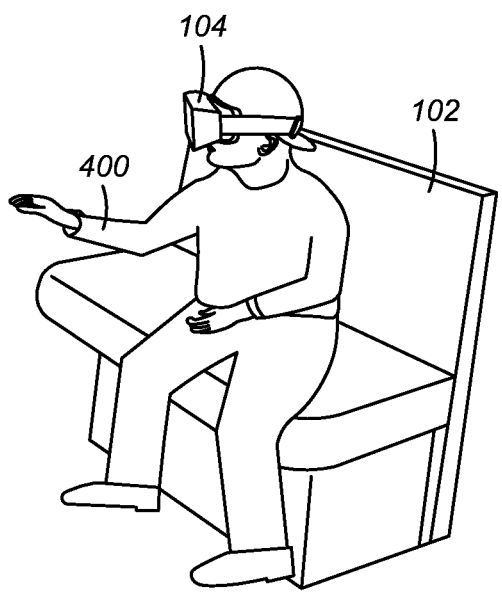

Notably, the tree 302 and sign 304 appear to move closer to the car as time progresses, giving the rider the visual impression that the car is moving forward. To accompany the visually perceived motion, the virtual reality ride system 100 includes a dynamic platform 102 that can move to create physical sensations representative of or associated with the virtual events occurring in the virtual environment. FIGS. 4A-4B depict an isolated view of the exemplary dynamic platform 102, which includes a bench. As shown in FIG. 4B, a rider 400 may sit on the bench while viewing the virtual environment through headset 104.

The dynamic platform 102 may translate, rotate, and/or vibrate in synchronization with the displayed video to apply forces that simulate what a rider would feel if he or she were actually moving according to what is being displayed or experiencing the events occurring in the virtual environment. The dynamic platform may translate, rotate, and/or vibrate along one or more axes, such as the x, y, and/or z axes indicated in FIG. 4A. For example, in the virtual environment displayed in FIGS. 3A-3C, the dynamic platform 102 may provide tactile feedback by vibrating, translating, and/or tilting to simulate the forces due to accelerations of the car caused by, for example, passing over bumps in the road, going around a turn, or starting or stopping.

Figure 5A:
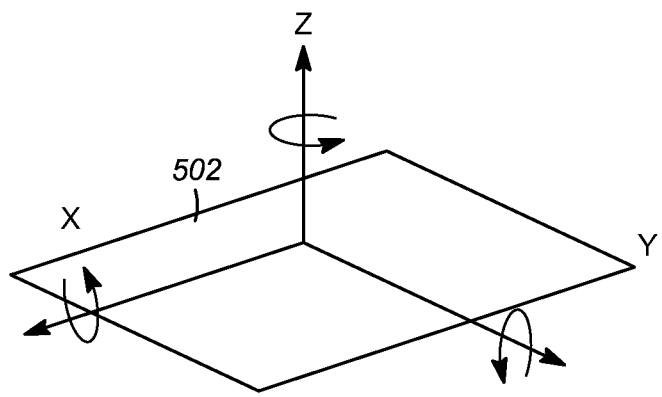
FIGS. 5A-5B depict another exemplary embodiment of a dynamic platform.
Figure 5B:
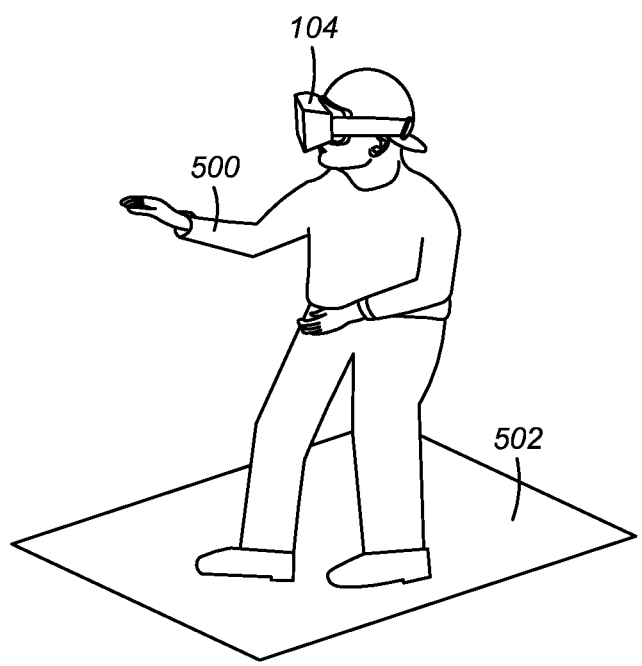

It should be recognized that the dynamic platform 102 may include another type of seat instead of a bench, such as a chair, kneeling chair, stool, pedestal, or the like. Alternatively, the dynamic platform may include a dynamic base, mat, floor, or the like upon which a rider might stand. FIG. 5A depicts an embodiment of a dynamic platform 502 that includes a movable base. FIG. 5B depicts the rider 500 standing on the movable base and wearing headset 104.

The movements that simulate events occurring in the virtual environment may be sufficient to avoid any disconnect between the motion perceived by the visual and vestibular systems, and therefore prevent motion sickness. In some embodiments, however, the dynamic platform may provide movements specifically for the purpose of reducing the amount of motion sickness experienced by the rider. The platform may produce low-frequency vibrations that stimulate the vestibular system, but do not represent or simulate motion associated with virtual events. In some embodiments, the low-frequency vibrations may be unrelated to any event in the virtual environment.

Turning again to FIGS. 3A-3C as an example, if the road is smooth and the car is not accelerating or decelerating (e.g., speeding up, slowing down, making a turn, etc.), then there may be no physical motion associated with the virtual movement of the car, in which case, the dynamic platform may not provide any motion. Without physical motion, however, the rider may experience motion sickness due to the inconsistency between the visually perceived motion of the car and the lack of motion sensed by the vestibular system.

The virtual reality ride system may attempt to compensate for this disconnect by causing the dynamic platform to vibrate or oscillate at a low frequency. The dynamic platform may vibrate at a frequency between approximately 5 Hz and 70 Hz by, for example, translating and/or rotating around one or more of the axes shown in FIG. 4A. The frequency may be fixed at a particular value within this band or modulated over time. In one embodiment, the vibrations have a frequency of approximately 50 Hz. The amplitude of the vibrations may also be fixed at a particular value or modulated over time. The amplitude may be large enough to stimulate the vestibular system of a rider interacting with the dynamic platform (e.g., sitting or standing on the platform). The amplitude required to stimulate the vestibular system may vary with frequency. In addition, if a rider is sitting or standing upright, vibrations caused by vertical displacement of the platform may be transferred more efficiently to the rider's head, and thus to the vestibular system, compared to horizontal motion, which may be absorbed by the lower body.

The low-frequency vibrations described above may be provided throughout an entire virtual experience or, alternatively, during selected portions. For example, the dynamic platform may only vibrate when the platform is not making other movements associated with virtual events or when the video shows that the rider is moving.

In some embodiments, the rider may be able to hear and/or feel the low-frequency vibrations intended to reduce motion sickness. Although the human ear is generally less sensitive to low frequencies than to high frequencies, the audible frequency range for the average human varies from about 20 Hz to about 20,000 Hz. For example, a common threshold for hearing at 70 Hz is about 35 dB of sound pressure (with reference to 20 micro-Pascal). Also, tones between 4 Hz and 16 Hz may be perceived by the body's sense of touch if the amplitude is large enough. Accordingly, there may be combinations of frequency and amplitude within the operating range of the dynamic platform that can be heard and/or felt by an average human.

In other embodiments, the frequency and amplitude of the vibration may be sufficient to stimulate the vestibular system but otherwise be unnoticeable to the rider. Despite the body's ability to hear and feel some low-frequency vibrations, the dynamic platform may produce vibrations that are perceived by the vestibular but cannot be heard or felt by the rider, or that do not fully correspond to the motion that is expected based on the rider's visual perception. At such frequencies, even if the rider may be unable to hear or feel the vibration, the vestibular system still senses the motion and causes the level of inconsistency between the visual and vestibular systems to be reduced or eliminated. Accordingly, the virtual reality ride system may reduce, postpone, or eliminate motion sickness without distracting the rider. For example, referring back to FIGS. 3A-3C, the system and method described above may allow the rider to experience riding along a perfectly smooth road at a constant speed, but without any motion sickness.

It should also be recognized that, although the virtual reality ride system is described above as being used by only one rider, the system may be configured for an arbitrary number of riders, each using his or her own headset. Furthermore, in one embodiment, the riders all share a common physical space and a common virtual space.

Furthermore, the system is not limited to any particular virtual environment. For example, the virtual experience may include flying on Santa's sleigh to the North Pole, riding on the back of an imaginary creature through the sky, taking a jeep through a safari, or other real or imaginary virtual experiences.

It should also be recognized that low-frequency vibrations may also be used to reduce or prevent motion sickness in simulator or virtual reality systems that incorporate other types of displays instead of or in addition to headsets. Alternative displays may include images projected onto a screen or a wall, computer monitors, televisions, or the like. In addition, the low-frequency techniques described above may not be limited to virtual and simulated environments. For example, low-frequency vibrations may also be used to reduce or prevent motion sickness in real-world environments such as in a car, plane, or boat.

Figure 6:
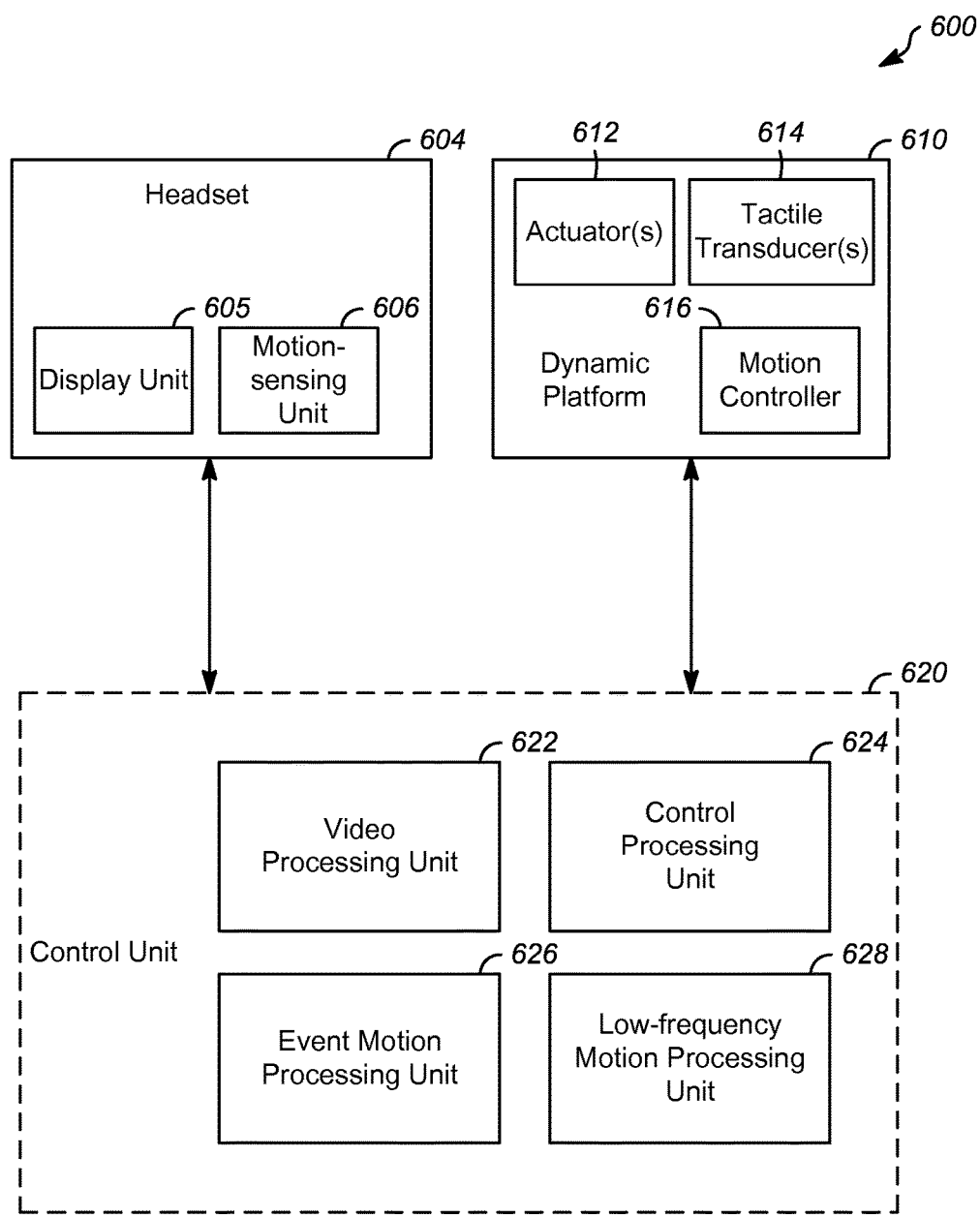
FIG. 6 depicts a block diagram of an exemplary virtual reality ride system.

Turning now to FIG. 6, an exemplary architecture of a virtual reality ride system 600 is described. FIG. 6 depicts a block diagram of an embodiment of the virtual reality ride system 600 including a headset 604 and dynamic platform 610, which are each connected to control unit 620. The headset 604 may include a display unit 605 and a motion-sensing unit 606 similar to those discussed above with respect to FIGS. 2A-2B.

The dynamic platform 610 may include one or more actuators 612 and one or more tactile transducers 614 controlled by a motion controller 616 to produce the motions of the dynamic platform 610. The actuators 612 may be motors that produce relatively large-scale motions associated with events in the virtual environment using electrical, hydraulic, pneumatic, or another type of energy. The tactile transducers 614 may provide vibrations that simulate or represent associated events in the virtual environment as well as vibrations unrelated to events in the virtual environment that do not necessarily simulate or represent any particular event. The tactile transducers 614 may include, for example, low-frequency transducers that provide low-frequency vibration with the characteristics described above for reducing motion sickness.

Figure 7:
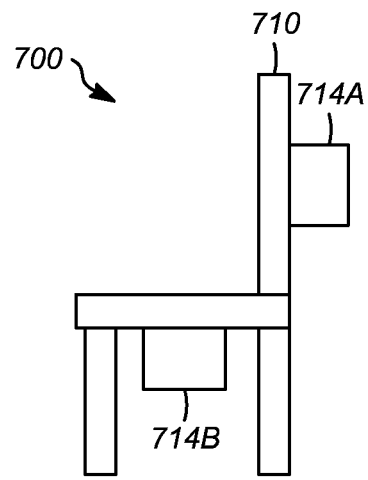
FIG. 7 depicts an exemplary embodiment of a dynamic platform.
Figure 8:
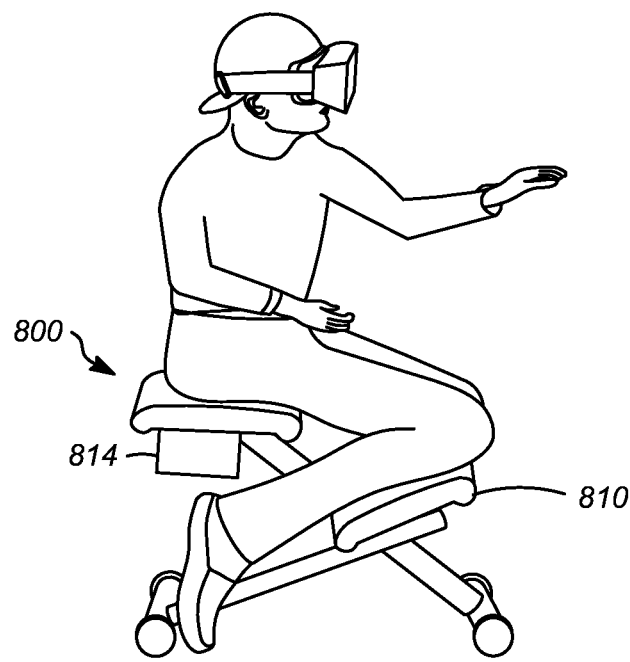
FIG. 8 depicts another exemplary embodiment of a dynamic platform.

The tactile transducers 614 may be incorporated into the dynamic platform 610 in various ways. FIGS. 7-8 depict two exemplary embodiments of a dynamic platform having one or more transducers. In FIG. 7, the dynamic platform 700 includes a chair 710 with a transducer 714A attached to the rear side of the backrest and a transducer 714B attached underneath the seat. In FIG. 8, the dynamic platform 800 includes a kneeling chair 810 with a transducer 814 mounted to the underside of the seat portion of the chair. The transducers 714A, 714B, and 814 may each vibrate to simulate forces associated with virtual events or produce other low-frequency vibrations to reduce motion sickness. In some embodiments, exemplary dynamic platforms 700 and 800 may not include actuators, in which case the transducers provide the only source of movement.

Turning again to FIG. 6, the motion controller 616 may include one or more processors, signal generators, or input/output devices that send motion commands and/or receive feedback from the actuators 612 and/or tactile transducers 614.

Control unit 620 may include one or more video processing unit 622, control processing unit 624, event motion processing unit 626, and low-frequency motion processing unit 628. The control unit 620 may be physically located within the dynamic platform 610 or placed in a separate location. The video processing unit 622 may provide video for the headsets 604. For example, video may be provided to the headsets 604 directly from the video processors 622, through the control processor 624, or through another processor in the control unit 620.

In one embodiment, the video processing unit 622 performs render processing that generates and renders video images of an animated virtual environment. In embodiments with more than one headset 604, the video processor(s) 622 may render an individual view of the virtual environment for each headset 604 based on the position and orientation of the headset 604. In some embodiments, multiple video processing units 622 may be slaved together by the control processing unit 624 so that events in the virtual environments occur at the same time for all riders.

The event motion processing unit 626 may determine motions associated with events that occur in the virtual environment and generate data representing those event-based motions. The event motion processing unit 626 may generate motion commands to be passed to the dynamic platform 610. Alternatively, it may provide the data representing the event-based motions to the control processing unit 624 or the motion controller 616, which convert the data into motion commands for the actuators 612 or the tactile transducers 614.

The low-frequency motion processing unit 628 may determine low-frequency vibrations unrelated to events in the virtual environment for the purpose of reducing motion sickness. The low-frequency motion processing unit 628 may generate data representing the low-frequency vibrations, which may include, for example, parameters such as amplitude, frequency, or duration. The low-frequency motion processing unit 628 may generate motion commands to be passed to the dynamic platform 610. Alternatively, it may provide the data representing the vibrations to the control processing unit 624 or the motion controller 616, which convert the data into motion commands for the actuators 612 or the tactile transducers 614.

The control processing unit 624 may coordinate the video displayed to the rider with the motion of the dynamic platform 610. The control processing unit 624 may send or receive data from any of the headsets 604, video processing units 622, event motion processing unit 626, low-frequency motion processing unit 628, motion controller 616, actuators 612, and tactile transducers 614. For example, the control processing unit 624 may provide the video processing unit 622 with data related to elements or events in the virtual environment (e.g., scenery, character motion, or the like). It may also provide the motion controller 616 with motion commands associated with the virtual events, such as those determined by the event motion processing unit 626, as well as motion commands unrelated to virtual events, such as those determined by the low-frequency motion processing unit 628 for reducing motion sickness.

The control unit 620 may include one or more processors that implement the functions of the video processing unit 622, control processing unit 624, event motion processing unit 626, and low-frequency motion processing unit 628. It should be recognized that the processing performed by the units may be performed by a single processor or distributed among more than one processor. There are various ways in which the processing may be distributed. In one embodiment, each unit includes one or more processors that implement the functions of that unit. In another embodiment, a processor may perform part or all of the processing for more than one unit.

Figure 9:
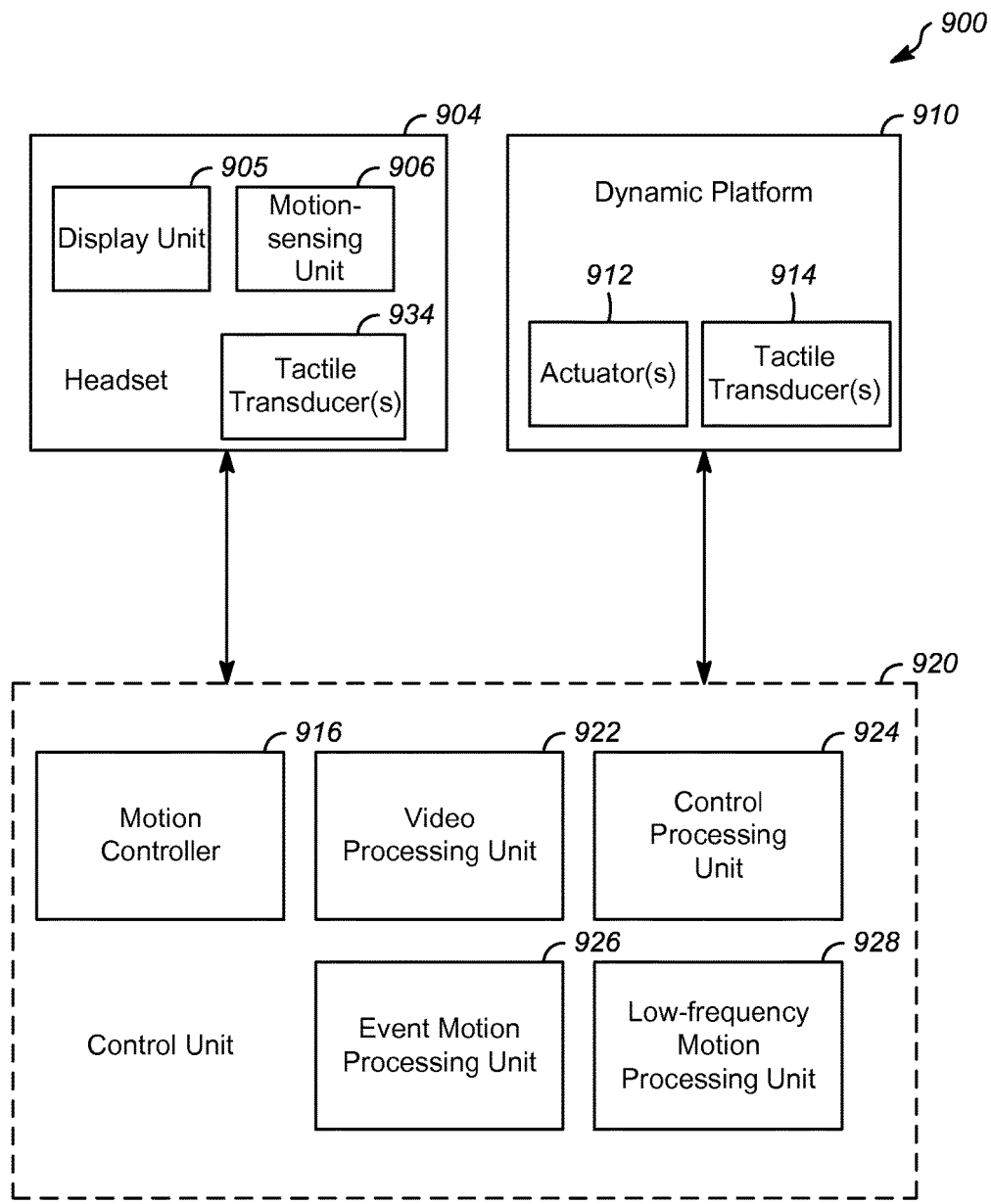
FIG. 9 depicts a block diagram of another exemplary virtual reality ride system.

In addition, it should be recognized that virtual reality ride system 600 is just one exemplary embodiment and that various alternative configurations are possible. FIG. 9 depicts another exemplary architecture of a virtual reality system 900, which is similar to system 600 except that the motion controller 916 is included in the control unit 920 and headset 904 includes at least one tactile transducer 934. The transducer 934 may be attached to the outside of the headset or integrated into the housing of the headset.

Figure 10:
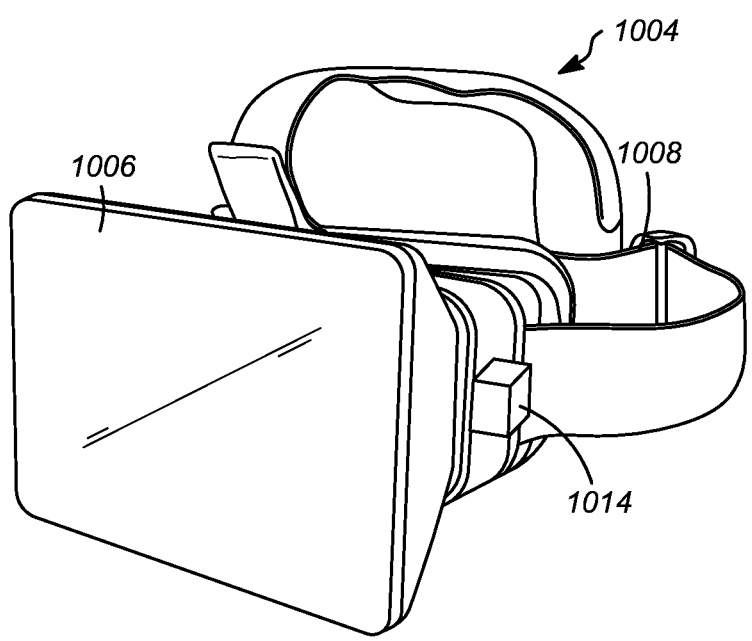
FIG. 10 depicts an exemplary embodiment of a virtual reality headset including a tactile transducer.

FIG. 10 depicts an exemplary headset 1004 with transducer 1014 connected to the side of the housing 1006. Including a transducer that produces low-frequency vibrations at the headset may reduce motion sickness more effectively and efficiently, as the transducer is located closer to the vestibular system, therefore allowing the transducer to be smaller or operate at lower amplitude. A smaller transducer may weigh less, cost less, and require less power. Including the transducer in the headset may also allow for a portable system that can reduce motion sickness without the need for a dynamic platform.

Figure 11:
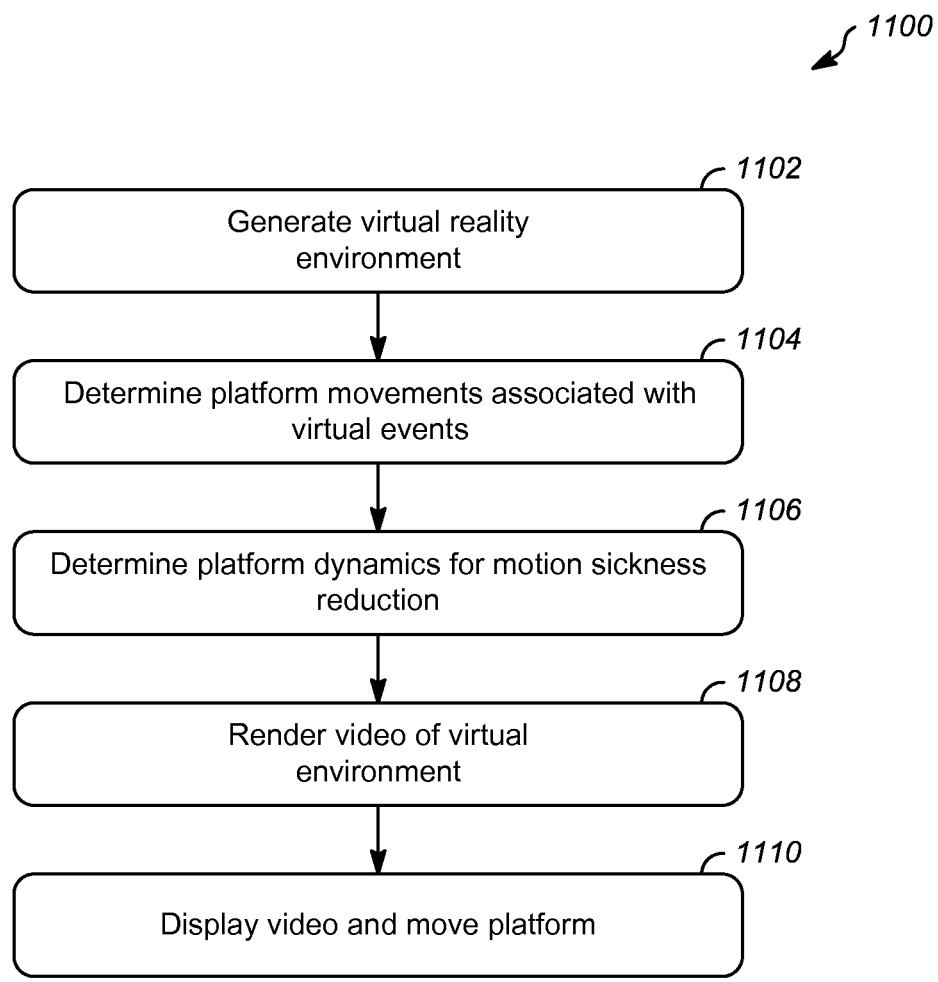
FIG. 11 depicts an exemplary process for operating a virtual reality ride system.

Turning now to FIG. 11, an exemplary process performed by a virtual reality ride system is described. In step 1102, the system generates a virtual environment. As mentioned above, the virtual environment may include animated assets such as characters, objects, scenery, and the like. Prior to beginning the ride, assets included in the environment, along with their initial state, may be loaded onto the control processor, which then determines updated positions of the assets based on motion models.

In step 1104, platform movements associated with events occurring in the virtual environment are determined. As mentioned above, the dynamic platform 102 may rotate and/or translate to apply forces that simulate what the rider would feel if he or she were actually in a real version of the virtual environment. Thus, the system may determine which virtual events have a corresponding motion, and the platform response associated with each event.

In step 1106, platform dynamics for reducing motion sickness are determined. For example, as in the "smooth road" example above, there may be times in the virtual environment in which it appears that the rider is moving but there is no platform motion, resulting in disagreement between the motion perceived by the visual system and the vestibular system. Accordingly, it may be determined that the platform should produce low-frequency vibrations at times when a disconnect is likely to occur to attempt to reduce effects of motion sickness. Alternatively, it may be determined that low-frequency vibrations should be provided throughout the entire ride, or intermittently according to some other pattern or criteria. For example, the system may produce low-frequency vibrations when the platform would otherwise be stationary, or simultaneous with motions associated with virtual events determined in step 1104. The system may determine the amplitude and frequency of the vibrations, as well as any changes or modulation in the amplitude and/or frequency over time.

In step 1108, video images of the virtual environment are rendered. Each frame of video is rendered based on a particular perspective of the virtual environment generated in step 1102. The perspective may be based on the location and/or orientation of a corresponding headset. For example, when the headset is facing upward, indicating the rider is looking overhead, the system may render a view of the sky in the virtual environment. The information required to render the proper perspective may be provided to the rendering processor from the headset itself or from the control processor.

In step 1110, video (as rendered in step 1108) is displayed through the headset and the platform is moved (as determined in steps 1104 and 1106). The video and motion are synchronized such that platform movements occur at the same time as their corresponding virtual events in the video, and low-frequency vibrations are provided at the determined times.

It should be recognized that certain steps described in process 1100 may be repeated or are not necessarily performed in the order shown in FIG. 11. For example, rendering of the video of the virtual environment in step 1108 may be performed prior to or in parallel with determination of the movements in steps 1104 and 1106. In some embodiments, the low-frequency vibrations may also be determined or adjusted during the virtual reality experience. On-the-fly determination may be advantageous for embodiments in which a user has control over movements or events in the virtual environment, such as, for example, a flight simulator or the like.

In other embodiments, the movements associated with virtual events, or the low-frequency vibrations for reducing motion sickness, may be determined prior to beginning the virtual reality experience. This may be advantageous for predetermined virtual experiences in which the user has no control over the movement or events that occur in the virtual environment (such as a virtual roller coaster ride, or the like) as it may reduce the computational resources required while running the system.

For example, a virtual experience may include a prerecorded audio soundtrack that includes music and/or sound effects. The audio output, or some portion thereof, may be fed to the transducers to provide low-frequency vibrations that stimulate the vestibular system during the virtual experience. The audio sent to the transducers may be modified or supplemented to achieve the desired motion sickness reducing effects. For example, the low-frequency portions of the soundtrack (e.g., the bass frequencies that would be provided to a subwoofer speaker) may be amplified and input into the transducer. The soundtrack may include sound effects and music synchronized with events in the virtual environment. Additional signals may be added to the soundtrack to produce low-frequency vibrations at times when the soundtrack does not provide vibrations that are sufficient to stimulate the vestibular system. Such times may include motion events that have no associated sound effects or that have associated sound effects without low-frequency components.

Figure 12:
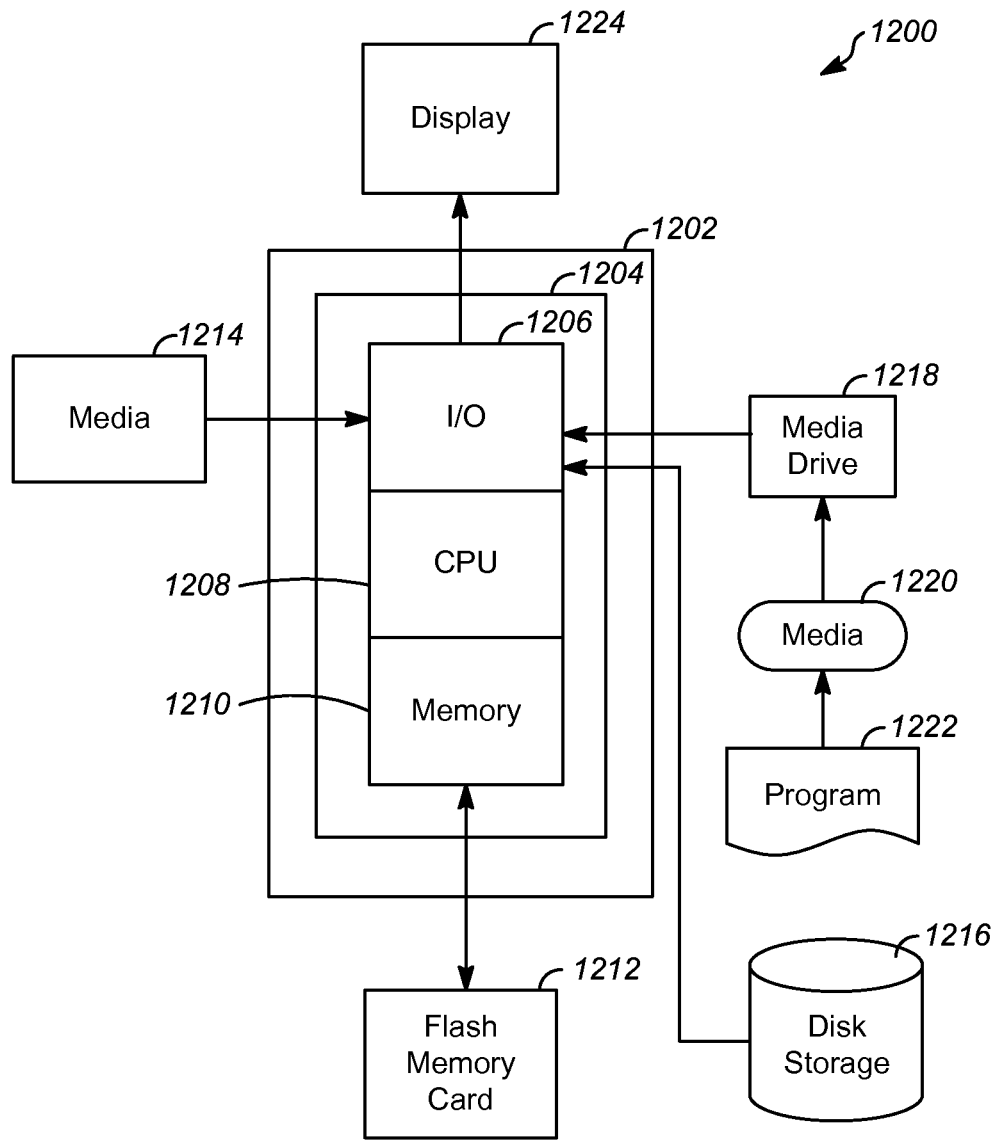
FIG. 12 depicts an exemplary computing system.

Turning now to FIG. 12, components of an exemplary computing system 1200, configured to perform any of the above-described processes, are depicted. In some embodiments, the control unit, video processors, rendering processors, control processors, and/or motion controllers described above may include some or all of the elements of computing system 1200. Computing system 1200 may include, for example, a processor, memory, storage, and input/output devices (e.g., monitor, keyboard, stylus, drawing device, disk drive, Internet connection, etc.). However, computing system 1200 may include circuitry or other specialized hardware for carrying out some or all aspects of the processes. In some operational settings, computing system 1200 may be configured as a system that includes one or more units, each of which is configured to carry out some aspects of the processes either in software, hardware, or some combination thereof.

In computing system 1200, the main system 1202 may include a motherboard 1204 with a bus that connects an input/output ("I/O") section 1206, one or more central processing unit ("CPU") 1208, and a memory section 1210, which may have a flash memory card 1212 related to it. Memory section 1210 may contain computer-executable instructions and/or data for carrying out at least portions of process 1100. The I/O section 1206 may be connected to display 1224, a keyboard 1214, a disk storage unit 1216, and a media drive unit 1218. The media drive unit 1218 can read/write a non-transitory computer-readable storage medium 1220, which can contain programs 1222 and/or data.

Additionally, a non-transitory computer-readable storage medium can be used to store (e.g., tangibly embody) one or more computer programs for performing any one of the above-described processes by means of a computer. The computer program may be written, for example, in a general-purpose programming language (e.g., Pascal, C, C++, Java, or the like) or some specialized application-specific language.

The foregoing descriptions of specific embodiments have been presented for purposes of illustration and description. They are not intended to be exhaustive or to limit the scope of the claims to the precise forms disclosed, and it should be understood that many modifications and variations are possible in light of the above teaching.

We claim:

1. A virtual reality ride system comprising:
   a headset including a display unit configured to display a video of an animated virtual environment;
   a dynamic platform; and
   a control unit including one or more processors configured to:
   render the video of the virtual environment;
   generate first data based on events that occur in the virtual environment, wherein the first data represents motions corresponding to the events in the virtual environment; and
   generate second data representing low-frequency vibrations, wherein the low-frequency vibrations are unrelated to the events in the virtual environment;
   wherein the dynamic platform is configured to, while the headset is displaying the rendered video of the virtual environment, use the first data and the second data to:
   move, based on the first data, in synchronization with the display of the rendered video of the virtual environment, wherein the movement of the dynamic platform based on the first data simulates the motions corresponding to the events in the virtual environment; and
   move, based on the second data, wherein the movement of the dynamic platform based on the second data includes the low-frequency vibrations and is unrelated to events in the displayed video of the virtual environment,
wherein the low-frequency vibrations include a frequency between about 5 Hz and 70 Hz, and
wherein the dynamic platform is configured to move based on the second data only when the dynamic platform is not moving based on the first data.

2. The virtual reality ride system of claim 1, wherein the low-frequency vibrations are not perceptible to a human sense of hearing.

3. The virtual reality ride system of claim 1, wherein the low-frequency vibrations are not perceptible to a human sense of touch.

4. The virtual reality ride system of claim 1, wherein the video is three-dimensional.

5. The virtual reality ride system of claim 1, wherein the video shows a first-person perspective of the virtual environment.

6. The virtual reality ride system of claim 1, wherein the dynamic platform is a seat.

7. The virtual reality system of claim 1, wherein the headset is configured to produce the low-frequency vibrations unrelated to events in the displayed video of the virtual environment.

8. A method of generating a virtual reality ride, the method comprising:
rendering a video of an animated virtual environment, the video including events in the virtual environment;
determining movements for a dynamic platform based on the events that occur in the virtual environment, wherein the movements correspond to the events in the virtual environment;
determining low-frequency vibrations for the dynamic platform, wherein the low-frequency vibrations have a frequency between about 5 Hz and 70 Hz, and wherein the low-frequency vibrations are unrelated to the events in the virtual environment;
displaying the video on a display; and
moving the dynamic platform, wherein:
the movement of the dynamic platform based on the determined movements is in synchronization with the video of the virtual environment and simulates the motions corresponding to the events in the virtual environment, and
the movement of the dynamic platform based on the low-frequency vibrations occurs only when the dynamic platform is not moving based on the determined movements, and includes the low-frequency vibrations and is unrelated to events in the displayed video of the virtual environment.

9. The method of claim 8, wherein the low-frequency vibrations are not perceptible to a human sense of hearing.

10. The method of claim 8, wherein the low-frequency vibrations are not perceptible to a human sense of touch.

11. The method of claim 8, wherein the video is three-dimensional.

12. The method of claim 8, wherein the video shows a first-person perspective of the virtual environment.

13. The method of claim 8, wherein the dynamic platform is a seat.

14. The method of claim 8, further comprising:
moving a headset, wherein the headset includes the display displaying the video of the animated virtual environment and is configured to produce the low-frequency vibrations unrelated to events in the displayed video of the virtual environment.

15. A non-transitory computer-readable storage medium comprising computer-executable instructions for generating a virtual reality ride, the computer-executable instructions comprising instructions for:
rendering a video of an animated virtual environment, the video including events in the virtual environment;
determining movements for a dynamic platform based on the events that occur in the virtual environment, wherein the movements correspond to the events in the virtual environment;
determining low-frequency vibrations for the dynamic platform, wherein the low-frequency vibrations have a frequency between about 5 Hz and 70 Hz, and wherein the low-frequency vibrations are unrelated to the events in the virtual environment;
displaying the video on a display; and
moving the dynamic platform, wherein:
the movement of the dynamic platform based on the determined movements is in synchronization with the video of the virtual environment and simulates the motions corresponding to the events in the virtual environment, and
the movement of the dynamic platform based on the low-frequency vibrations occurs only when the dynamic platform is not moving based on the determined movements, and includes the low-frequency vibrations and is unrelated to events in the displayed video of the virtual environment.

16. The computer-readable storage medium of claim 15, wherein the low-frequency vibrations are not perceptible to a human sense of hearing.

17. The computer-readable storage medium of claim 15, wherein the low-frequency vibrations are not perceptible to a human sense of touch.

18. The computer-readable storage medium of claim 15, wherein the video is three-dimensional.

19. The computer-readable storage medium of claim 15, wherein the video shows a first-person perspective of the virtual environment.

20. The computer-readable storage medium of claim 15, wherein the dynamic platform is a seat.

21. The computer-readable storage medium of claim 15, wherein the computer-executable instructions further comprise instructions for:
moving a headset, wherein the headset includes the display displaying the video of the animated virtual environment and is configured to produce the low-frequency vibrations unrelated to events in the displayed video of the virtual environment.

* * * * *